US012203920B2

(12) United States Patent
Riverin (10) Patent No.: US 12,203,920 B2
(45) Date of Patent: Jan. 21, 2025

(54) MULTI-ZONE MAGNETIC CHIP DETECTOR

(71) Applicant: PRATT & WHITNEY CANADA CORP., Longueuil (CA)

(72) Inventor: Guy Riverin, Montreal (CA)

(73) Assignee: PRATT & WHITNEY CANADA CORP., Longueuil (CA)

(*) Notice: Subject to any disclaimer, the term of this patent is extended or adjusted under 35 U.S.C. 154(b) by 567 days.

(21) Appl. No.: 17/525,446

(22) Filed: Nov. 12, 2021

(65) Prior Publication Data

US 2023/0152297 A1 May 18, 2023

(51) Int. Cl.
*G01N 33/28* (2006.01)
*F01M 1/10* (2006.01)
(Continued)

(52) U.S. Cl.
CPC ........... *G01N 33/2858* (2013.01); *F01M 1/10* (2013.01); *F01M 11/10* (2013.01); *F16N 29/00* (2013.01);
(Continued)

(58) Field of Classification Search
CPC ........... G01N 33/2858; G01N 15/0656; G01N 33/2888; G01N 2015/0053; G01N 15/1031; F01M 1/10; F01M 11/10; F01M 2001/1042; F01M 2011/144; F01M 2250/60; F16N 29/00; F16N 2200/04;
(Continued)

(56) References Cited

U.S. PATENT DOCUMENTS 4,008,464 A 2/1977 Hobbie
5,264,832 A 11/1993 Parmer
(Continued)

FOREIGN PATENT DOCUMENTS

CN 110108623 A 8/2019
DE 102009000077 B4 4/2011

OTHER PUBLICATIONS

European Patent Office, Communication re. extended European search report for European patent application 10. 22207347.0, Mar. 6, 2023.
English translation of China patent document No. CN110108623 dated Aug. 9, 2019, https://patents.google.com/patent/CN110108623A/en?oq=CN110108623A, accessed on Jun. 10, 2021.

*Primary Examiner* — Giovanni Astacio-Oquendo
(74) *Attorney, Agent, or Firm* — Norton Rose Fulbright Canada LLP (57) ABSTRACT

Magnetic chip detectors and associated for detecting metallic chips in engine fluid of an engine are provided. A magnetic chip detector includes first and second magnetic chip capture zones. The first magnetic chip capture zone includes a first electrically conductive terminal spaced apart from a second electrically conductive terminal to define a first chip-receiving gap therebetween. The second magnetic chip capture zone includes a third electrically conductive terminal and either the second electrically conductive terminal or a fourth electrically conductive terminal to define a second chip-receiving gap therebetween. The magnetic chip detector includes an electric circuit including both the first chip-receiving gap and the second chip-receiving gap. The electric circuit provides an output indicative of a chip detection by one or both of the first magnetic chip capture zone and the second magnetic capture zone.

20 Claims, 10 Drawing Sheets

(51) Int. Cl.
    *F01M 11/10*       (2006.01)
    *F16N 29/00*       (2006.01)
    *G01N 15/06*       (2006.01)
    *G01N 15/00*       (2006.01)

(52) U.S. Cl.
    CPC ..... *G01N 15/0656* (2013.01); *G01N 33/2888* (2013.01); *F01M 2001/1042* (2013.01); *F01M 2011/144* (2013.01); *F01M 2250/60* (2013.01); *F16N 2200/04* (2013.01); *F16N 2210/08* (2013.01); *G01N 2015/0053* (2013.01)

(58) Field of Classification Search
    CPC .... F16N 2210/08; F16N 2210/02; F16N 7/38; F16N 29/04; F16N 39/00
    USPC .......................................... 324/205, 204, 200
    See application file for complete search history.

(56) References Cited

U.S. PATENT DOCUMENTS

| | | | |
|---|---|---|---|
| 9,316,630 | B2 | 4/2016 | Hodgkinson et al. |
| 10,197,488 | B2* | 2/2019 | Youssef .................. G01V 3/02 |
| 11,066,950 | B2* | 7/2021 | Jean ....................... G01N 15/14 |
| 2002/0145530 | A1 | 10/2002 | Sato |
| 2009/0314064 | A1 | 12/2009 | Augros et al. |
| 2020/0340936 | A1 | 10/2020 | Sakurai et al. |
| 2021/0070474 | A1* | 3/2021 | Belhabib .............. G08B 21/182 |
| 2021/0263009 | A1 | 8/2021 | Shenouda |
| 2022/0099651 | A1* | 3/2022 | Padilla Martinez .... F01D 25/18 |
| 2023/0054919 | A1* | 2/2023 | Al-Khairy ............... F16N 29/00 |
| 2023/0147354 | A1* | 5/2023 | Carroll ................... F16N 39/02 |
| | | | 73/53.07 |

* cited by examiner

MULTI-ZONE MAGNETIC CHIP DETECTOR

TECHNICAL FIELD

The disclosure relates generally to health monitoring of engines, and more particularly to detecting chips in fluids of aircraft engines.

BACKGROUND

A magnetic chip detector is commonly found in a lubrication system of an aircraft engine to detect the presence of metallic chips in the lubricating fluid. The chip detector is immersed in the lubricating fluid so as to be exposed to the chips carried by the lubricating fluid. The presence of chips in the lubricating fluid may indicate a developing and/or impending mechanical problem exhibiting excessive wear of one or more components of the aircraft engine interacting with the lubrication system. When chips are collected by the chip detector, a gap between two electric terminals is eventually bridged so as to provide electric continuity and cause an indication (e.g., alarm) to be provided to an operator of the aircraft so that an appropriate action can be taken if necessary. The presence of metal chips in engine fluid can be indicative of a deteriorating engine health condition and it is desirable to improve chip detection in aircraft engines.

SUMMARY

In one aspect, the disclosure describes a multi-zone magnetic chip detector for detecting chips in lubricating fluid of an engine. The multi-zone magnetic chip detector comprises:
 a first magnetic chip capture zone including a first electrically conductive terminal spaced apart from a second electrically conductive terminal to define a first chip-receiving gap therebetween;
 a second magnetic chip capture zone including a third electrically conductive terminal and either the second electrically conductive terminal or a fourth electrically conductive terminal to define a second chip-receiving gap therebetween; and
 an electric circuit including both the first chip-receiving gap and the second chip-receiving gap, the electric circuit providing an output indicative of a chip detection by one or both of the first magnetic chip capture zone and the second magnetic capture zone.

In another aspect, the disclosure describes an aircraft engine comprising:
 a lubrication system for distributing lubricating fluid to one or more lubrication loads; and
 a multi-zone magnetic chip detector immersed in the lubricating fluid, the multi-zone magnetic chip detector including:
 a first magnetic chip capture zone including a first electrically conductive terminal spaced apart from a second electrically conductive terminal to define a first chip-receiving gap therebetween;
 a second magnetic chip capture zone including a third electrically conductive terminal and either the second electrically conductive terminal or a fourth electrically conductive terminal to define a second chip-receiving gap therebetween; and
 an electric circuit including both the first chip-receiving gap and the second chip-receiving gap, the electric circuit providing an output indicative of a chip detection by one or both of the first magnetic chip capture zone and the second magnetic capture zone.

In a further aspect, the disclosure describes a method of detecting metallic chips in engine fluid of an engine using a multi-zone magnetic chip detector including: a first magnetic chip capture zone defined between a first electrically conductive terminal and a second electrically conductive terminal; and a second magnetic chip capture zone defined between a third electrically conductive terminal and either the second electrically conductive terminal or a fourth electrically conductive terminal. The method comprises:
 when the multi-zone magnetic chip detector is immersed in engine fluid, receiving one or more metallic chips in one or both of the first magnetic chip capture zone and the second magnetic chip capture zone; and
 using an electric circuit including both the first magnetic chip capture zone and the second magnetic chip capture zone, generating an output indicative of a chip detection in the one or both of the first magnetic chip capture zone and the second magnetic capture zone.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

The present disclosure relates to systems and methods for detecting metallic chips in engine (e.g., lubricating, cooling) fluids. In some embodiments, the systems and methods described herein may help assess a condition of an engine by using one or more multi-zone magnetic chip detectors to reduce the probability of generating nuisance chip detections and associated annunciations or alarms. For example, the systems and methods described herein may reduce the probability of nuisance chip detections associated with the accumulation of acceptable smaller/fine magnetic debris/particles, commonly referred to as "fuzz" at a magnetic chip detector immersed in lubricating fluid. Some fuzz can be generated during the normal operation of an aircraft engine and may not necessarily be indicative of a developing or impending mechanical problem. For example, such fuzz can normally be generated during the initial period (e.g., a few hundred hours) of operation of an aircraft engine following initial entry into service or following extensive maintenance such as an overhaul. This initial period is also known as the engine's "break-in" period. Chip detections caused by the accumulation of the acceptable and relatively harmless fuzz, during the break-in period for example, oppose the design intent of the magnetic chip detector and are undesirable since they do not provide an accurate indication of a possible developing or impending problem.

Metallic chips that are carried by the lubricating fluid may be from metallic engine parts such as gear teeth or bearings for example. Some disc type magnetic chip detectors use one disk-shaped magnet placed in a non-conductive and non-magnetically permeable isolator with two conductive steel end caps which, in combination, create a single chip capture zone. When a metallic chip of a sufficient size is attracted to the capture zone by the magnet, the metallic chip bridges (e.g., short-circuits) the gap between the steel end caps to complete an electric circuit that includes the gap. A controller or other annunciation circuitry connected to the magnetic chip detector may detect this change in resistance caused by the metallic chip and indicate to a pilot of the aircraft via a cockpit indication the presence of one or more magnetic chips having been detected by the magnetic chip detector.

Magnetic chip detectors may use rare earth magnets that provide a relatively high capture efficiency. This can result in a high sensitivity of a magnetic chip detector, which may increase the probability of nuisance detections. For example, a magnetic chip detector with a single capture zone may function as an on/off switch and may trigger an annunciation based on a relatively harmless single metallic filament having been captured in the single capture zone. Once the chip detection is triggered by one or more chips, the pilot may be required to abort the mission mid-flight, return to the ground (e.g., base) as soon as possible, and remove (or have maintenance personnel remove) the magnetic chip detector for visual inspection. The visual inspection verifies whether significant debris has been collected by the magnetic chip detector and hence whether maintenance is required before the aircraft can be dispatched again. If the detection is triggered by an insignificant metallic filament or other insignificant metallic particle(s), such detection can be a nuisance to the pilot and/or aircraft operator.

In some embodiments, the magnetic chip detectors described herein may reduce the probability of single chip detections and other nuisance detection events. In some embodiments, the magnetic chip detectors described herein may reduce the probability of fuzz-induced nuisance detections. In some embodiments, the magnetic chip detectors described herein may provide an indication of a degree of contamination that allows a system to discriminate between harmless/tolerable contamination and gross contamination indicative of a developing and/or impending mechanical problem. In some embodiments, the magnetic chip detectors described herein may provide an ability to discriminate between small or large chips being detected.

In some embodiments, the magnetic chip detectors described herein may provide a more informative indication via a single interface, which may facilitate installation (e.g., retrofitting) into existing engines and associated controllers by not requiring an increased number of inputs to the controller or aircraft. In some embodiments, the magnetic chip detectors described herein may permit the monitoring of different regions of a fluid (e.g., lubrication, cooling) system of an aircraft engine via the single interface.

Aspects of various embodiments are described through reference to the drawings. Even though the description below is provided in relation to lubricating fluid, it is understood that some embodiments of the magnetic chip detectors, systems and methods described herein may also be used on other types of engine fluids such as engine coolant for example.

The term "connected" may include both direct connection (in which two elements that are connected to each other contact each other) and indirect connection (in which at least one additional element is located between the two elements).

The term "substantially" as used herein may be applied to modify any quantitative representation which could permissibly vary without resulting in a change in the basic function to which it is related.

Figure 1:
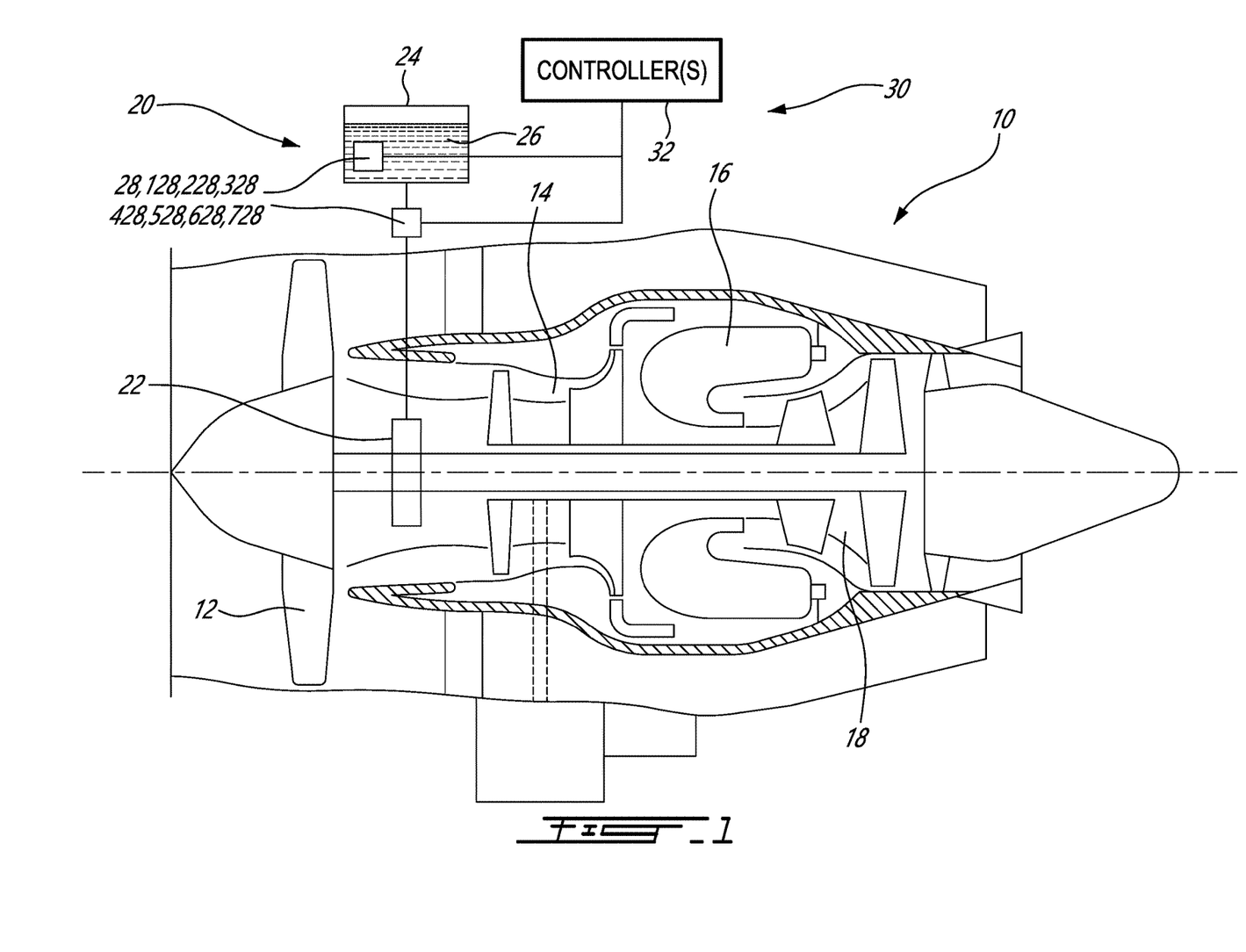
FIG. 1 is a schematic axial cross-section view of a turbofan gas turbine engine including a multi-zone magnetic chip detector as described herein.

FIG. 1 is a schematic axial cross-section view of aircraft engine 10 (referred hereinafter as "engine 10") of a turbofan gas turbine engine preferably provided for use in subsonic flight, generally comprising, in serial flow communication, fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Even though FIG. 1 shows engine 10 being of the turbofan type, it is understood that aspects of the present disclosure are also applicable to other (e.g., turboshaft, turboprop, internal combustion) types of aircraft engines.

Engine 10 may include lubrication (and/or other fluid) system 20 shown schematically and partially in FIG. 1. Lubrication system 20 may serve to lubricate, cool and clean one or more lubrication loads 22 such as bearings and gears of engine 10. Lubrication system 20 may include tank 24 and other components such as one or more pumps, one or more valves, and one or more filters. Tank 24 may be a reservoir containing a supply of lubricating fluid 26 such as oil for use by lubrication system 20. Lubrication system 20 may include one or more magnetic chip detectors (MCDs) 28. For example, lubrication system 20 may include a single MCD 28 or a plurality of MCDs 28 disposed at different locations within lubrication system 20. MCD 28 may be at least partially immersed in lubricating fluid 26 during operation. For example, MCD 28 be disposed inside tank 24, inside a gearbox, or in a scavenge line.

MCD 28 may be part of chip detection system 30 (referred hereinafter as "system 30") and may be associated with and/or may be part of engine 10. System 30 may include controller 32 or other detection circuitry operatively connected to MCD 28. In various embodiments, controller 32 may include or form part of a Full Authority Digital Engine Control (FADEC) which may, for example, include one or more digital computer(s) or other data processors, sometimes referred to as electronic engine controller(s) (EEC) and related accessories that control at least some aspects of performance of engine 10. Controller 32 may, for example, be configured to make decisions regarding the control of engine 10. Controller 32 may include one or more data processors and non-transitory machine-readable memory. Controller 32 may receive input(s) from MCD 28, perform one or more procedures or steps defined by instructions stored in the memory to generate output(s) such as triggering a suitable annunciation to a pilot of the aircraft for example. Various aspects of the present disclosure may be embodied as systems, devices, methods and/or computer program products.

Figure 2A:
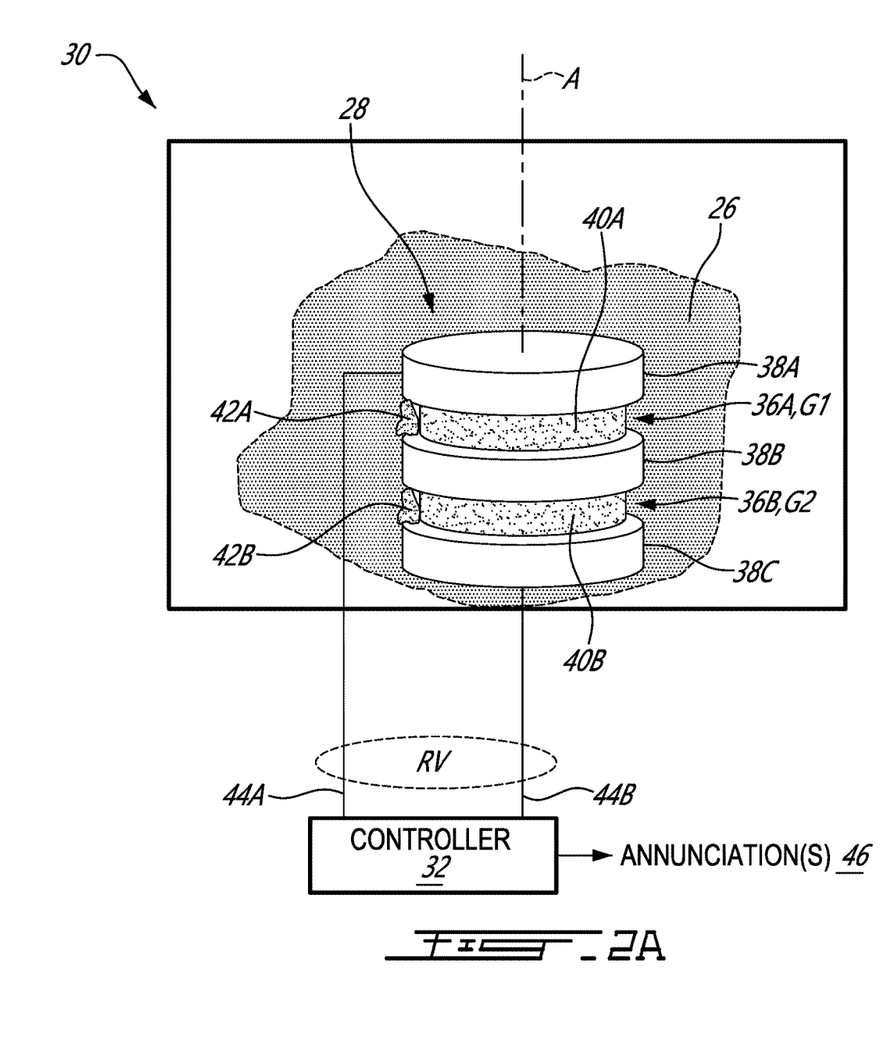
FIG. 2A is an exemplary schematic representation of the multi-zone magnetic chip detector of the engine of FIG. 1.
Figure 2B:
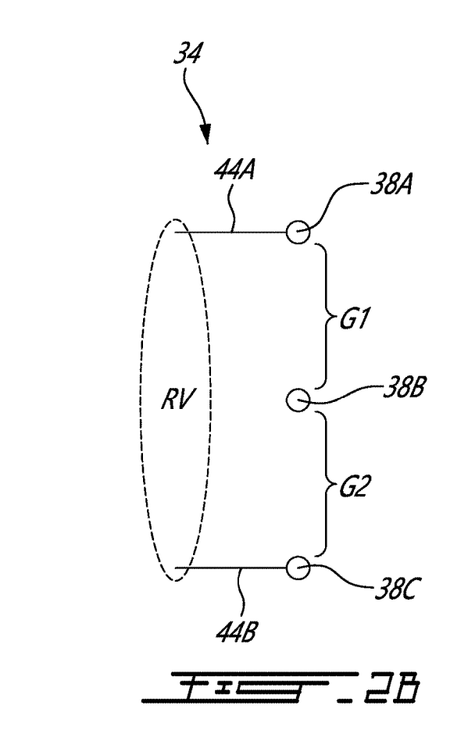
FIG. 2B is a schematic representation of an electric circuit associated with the multi-zone magnetic chip detector of FIG. 2A.

FIG. 2A is an exemplary schematic representation of MCD 28 shown a as part of chip detection system 30 of engine 10, and FIG. 2B is a schematic representation of electric circuit 34 associated with MCD 28. MCD 28 may include two or more magnetic chip capture zones 36A, 36B to thereby reduce the probability of single-chip and/or fuzz-induced nuisance detections. MCD 28 may include first capture zone 36A and second capture zone 36B. First capture zone 36A may include first electrically conductive terminal 38A (referred hereinafter as "first MCD terminal 38A") spaced apart from second electrically conductive terminal 38B (referred hereinafter as "second MCD terminal 38B") to define first chip-receiving gap G1 (referred hereinafter as "first gap G1") therebetween. Second capture zone 36B may include third electrically conductive terminal 38C (referred hereinafter as "third MCD terminal 380") spaced apart from second MCD terminal 38B to define second chip-receiving gap G2 (referred hereinafter as "second gap G2") therebetween. The size(s) of first gap G1 and of second gap G2 may be selected based on the chip sizes of interest. In some embodiments, the size(s) of first gap G1 and second gap G2 may be between 1/64" (0.4 mm) and 1/8" (3.2 mm) for example.

MCD 28 may be an axial disk-type magnetic chip detector. However, aspects of the present disclosure are also applicable to other types of magnetic chip detectors such as prong-type magnetic chip detectors as explained further below. For example, MCD 28 may include first magnet 40A disposed and retained between first MCD terminal 38A and second MCD terminal 38B. MCD 28 may include second magnet 40B disposed and retained between third MCD terminal 38C and second MCD terminal 40C. Suitable electrically non-conductive and non-magnetically permeable isolators (not shown) may be disposed between first magnet 40A and the respective first MCD terminal 38A and second MCD terminal 38B. First MCD terminal 38A and second MCD terminal 38B may be metallic (e.g., steel) end caps between which first magnet 40A is retained. Similarly, second magnet 40B may be disposed and retained between second MCD terminal 38B and third MCD terminal 38C. Suitable electrically non-conductive and non-magnetically permeable isolators (not shown) may be disposed between second magnet 40B and the respective second MCD terminal 38B and third MCD terminal 38C. Second MCD terminal 38B and third MCD terminal 38C may be metallic (e.g., steel) end caps between which second magnet 40B is retained. In some embodiments, second MCD terminal 38B may be common to both first capture zone 36A and second capture zone 36B and may be a double-sided end cap that is sandwiched between first magnet 40A and second magnet 40B.

In some embodiments, first magnet 40A, second magnet 40B, first MCD terminal 38A, second MCD terminal 38B, and third MCD terminal 38C may be disk-shaped and may be disposed in a coaxial manner along axis A. In some embodiments, first magnet 40A, second magnet 40B, first MCD terminal 38A, second MCD terminal 38B, and third MCD terminal 38C may be integrated/assembled into a single metallic chip detector that may be disposed in a single region of lubrication system 20 (shown in FIG. 1) of engine 10. For example, both first capture zone 36A and second capture zone 36B may be in fluid communication with each other during use when MCD 28 is immersed in lubricating fluid 26. MCD 28 could also be configured to define one or more additional capture zones by adding additional magnet(s) and end cap(s).

FIG. 2A also illustrates a situation where: first metallic chip 42A has been captured by first capture zone 36A and electrically bridges first gap G1; and second metallic chip 42B has been captured by second capture zone 36B and electrically bridges second gap G2.

Electric circuit 34 may include first output terminal 44A and second output terminal 44B together defining a single interface between MCD 28 and controller 32. As shown in FIG. 2B, electric circuit 34 may include both first gap G1 and second gap G2. Electric resistance value RV across first output terminal 44A and second output terminal 44B may serve as a single output communicated to controller 32 as an indication of whether or not a chip detection has occurred at MCD 28 and annunciation 46 is warranted. In various embodiments, first gap G1 and second gap G2 may be disposed in series as shown in FIG. 2B, or may be disposed in parallel in electric circuit 34. In some embodiments, first gap G1 and second gap G2 may be of substantially the same size. However, in other embodiments, first gap G1 and second gap G2 may be of different sizes depending on the sizes of first chip 42A and of second chip 42B that are of interest.

During operation of MCD 28 shown in FIGS. 2A and 2B when MCD 28 is immersed in lubricating fluid 26, resistance value RV may be high (e.g., open circuit) when neither or only one of first gap G1 and second gap G2 is electrically bridged by first chip 42A or second chip 42B. On the other hand, resistance value RV may be low (e.g., short circuit, near 0 ohm) when first gap G1 is electrically bridged by first chip 42A, and second gap G2 is electrically bridged by second chip 42B. Accordingly, the chip detection at MCD 28 may be detected by way of a change in resistance value RV which may be determined at controller 32. Upon detection of the change in resistance value RV that is indicative of a legitimate chip detection, controller 32 may initiate annunciation 46 which may alert a pilot of the aircraft and/or another interested party. Annunciation 46 may be visual (e.g., indicator light or message) or aural (e.g., tone or spoken message). It is understood that in some embodiments, controller 32 may be replaced by suitable analog circuitry that causes annunciation 46 upon first MCD terminal 38A and third MCD terminal 38C becoming electrically bridged by the presence of both first chip 42A and second chip 42B.

Figure 3A:
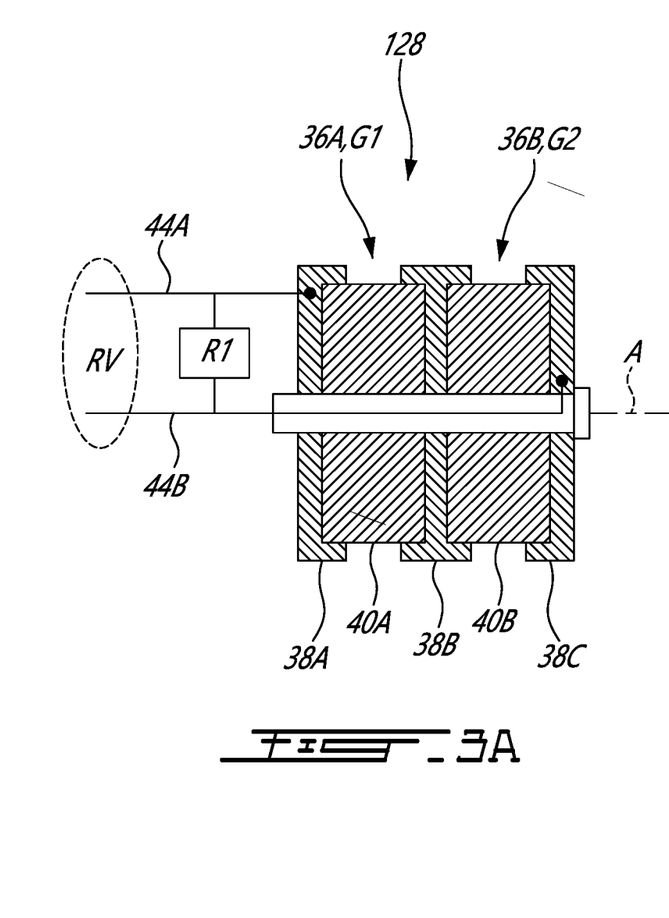
FIG. 3A is a schematic axial cross-section view of another exemplary multi-zone magnetic chip detector of the engine of FIG. 1.
Figure 3B:
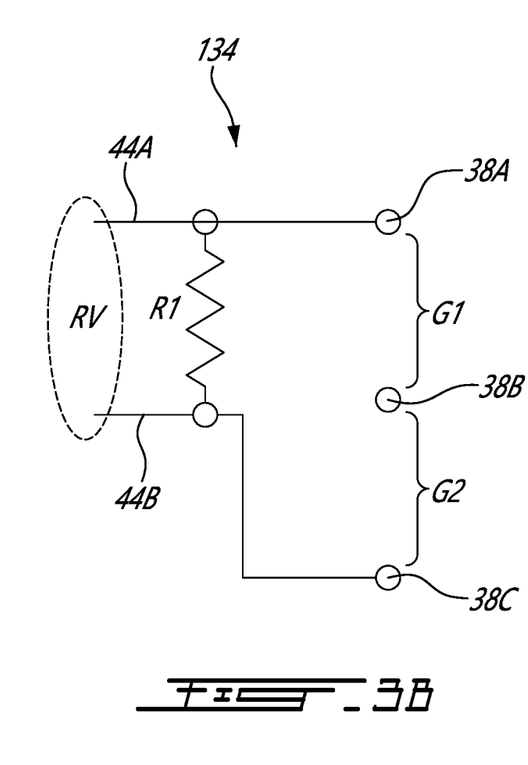
FIG. 3B is a schematic representation of an electric circuit associated with the multi-zone magnetic chip detector of FIG. 3A.

FIG. 3A is a schematic axial cross-section view of another exemplary multi-zone MCD 128 which may be part of chip detection system 30 of engine 10, and FIG. 3B is a schematic representation of electric circuit 134 associated with MCD 128. MCD 128 may have elements in common with MCD 28 described above and like elements are identified using like reference numerals. In contrast with MCD 28, MCD 128 may include shunt resistor R1 disposed in parallel with both first gap G1 and second gap G2. MCD 128 may also include first capture zone 36A, second capture zone 36B, and optionally one or more additional capture zones to thereby reduce the probability of single-chip and/or fuzz-induced nuisance detections. First capture zone 36A may include first MCD terminal 38A spaced apart from second MCD terminal 38B to define first gap G1 therebetween. Second capture zone 36B may include third MCD terminal 38C spaced apart from second MCD terminal 38B to define second gap G2 therebetween. MCD 128 may be an axial disk-type magnetic chip detector. In some embodiments, first gap G1 and second gap G2 may be of substantially the same size. However, in other embodiments, first gap G1 and second gap G2 may be of different sizes depending on the size of first chip 42A and of second chip 42B that are of interest. In various embodiments, first gap G1 and second gap G2 may be disposed in series as shown in FIG. 3B, or may be disposed in parallel in electric circuit 134.

During operation of MCD 128 shown in FIGS. 3A and 3B when MCD 128 is immersed in lubricating fluid 26, resistance value RV may the value of R1 (e.g., 2 k Ohm) when neither or only one of first gap G1 and second gap G2 is electrically bridged by first chip 42A or second chip 42B (shown in FIG. 2A). On the other hand, resistance value RV may be low (e.g., short circuit, near 0 ohm) when first gap G1 is electrically bridged by first chip 42A, and second gap G2 is electrically bridged by second chip 42B. Accordingly, the chip detection at MCD 128 may be detected by way of a change in resistance value RV which may be determined at controller 32. Upon detection of the change in resistance value RV that is indicative of a legitimate chip detection, controller 32 may initiate annunciation 46 which may alert a pilot of the aircraft and/or another interested party.

Figure 4A:
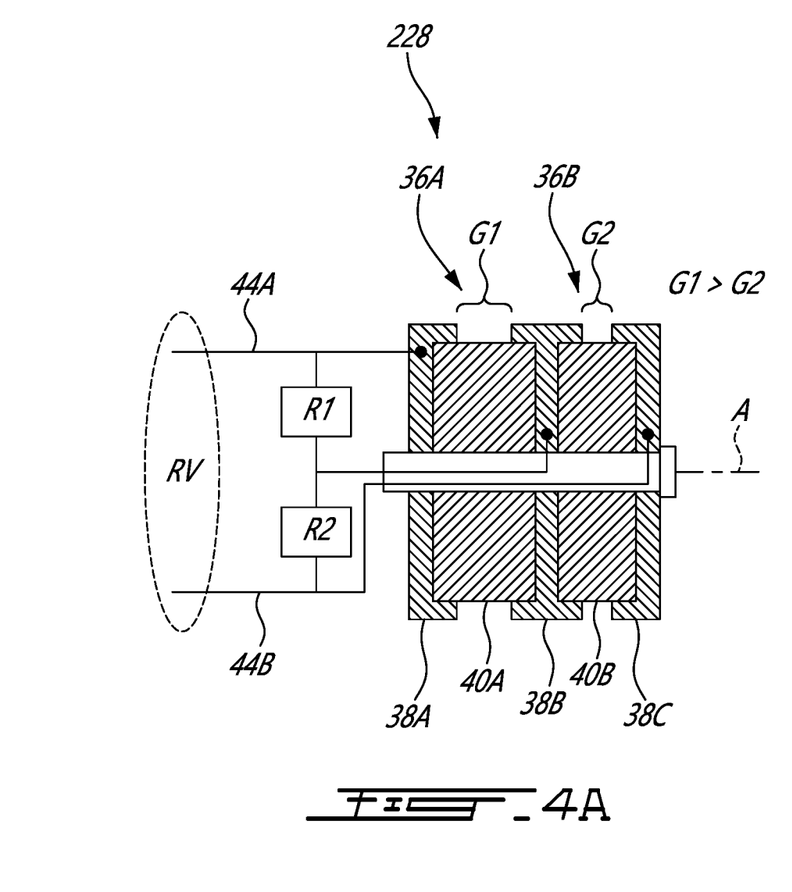
FIG. 4A is a schematic axial cross-section view of another exemplary multi-zone magnetic chip detector of the engine of FIG. 1.
Figure 4B:
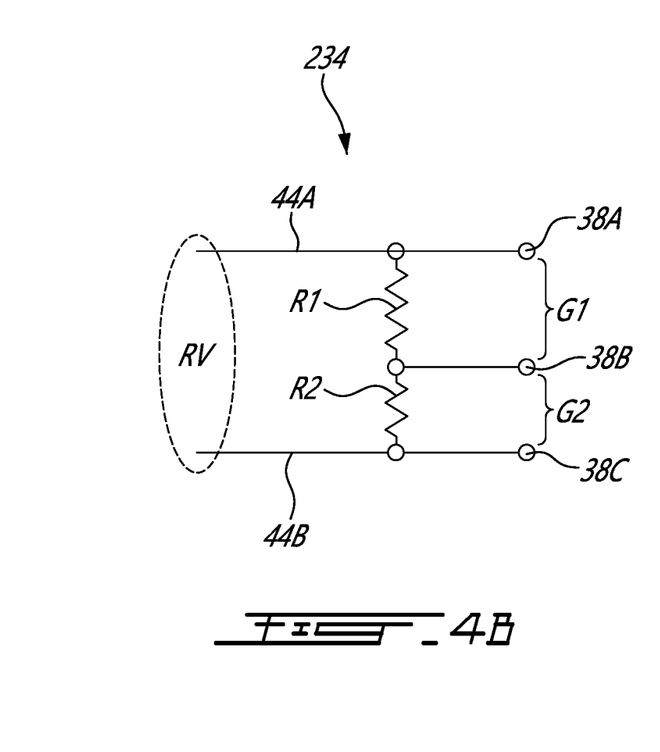
FIG. 4B is a schematic representation of an electric circuit associated with the multi-zone magnetic chip detector of FIG. 4A.

FIG. 4A is a schematic axial cross-section view of another exemplary multi-zone MCD 228 which may be part of chip detection system 30 of engine 10, and FIG. 4B is a schematic representation of electric circuit 234 associated with MCD 228. MCD 228 may have elements in common with other MCDs described above and like elements are identified using like reference numerals. In contrast with MCD 128, MCD 228 may include shunt resistor R1 disposed in parallel with first gap G1, and shunt resistor R2 disposed in parallel with second gap G2. Resistor R1 and resistor R2 may have different or substantially identical resistance values. Resistor R1 and resistor R2 may be disposed in series with each other in electric circuit 234.

MCD 228 may also include first capture zone 36A, second capture zone 36B, and optionally one or more additional capture zones. First capture zone 36A may include first MCD terminal 38A spaced apart from second MCD terminal 38B to define first gap G1 therebetween. Second capture zone 36B may include third MCD terminal 38C spaced apart from second MCD terminal 38B to define second gap G2 therebetween. MCD 228 may be an axial disk-type magnetic chip detector. In some embodiments, first gap G1 and second gap G2 may be of substantially the same size. However, as shown in FIGS. 4A and 4B, first gap G1 may be larger than second gap G2 so that G1>G2. First gap G1 and second gap G2 may be sized based on the size of first chip 42A and second chip 42B that are of interest. In various embodiments, first gap G1 and second gap G2 may be disposed in series as shown in FIG. 4B, or may be disposed in parallel in electric circuit 234.

During operation, the use of MCD 228 when MCD 228 is immersed in lubricating fluid 26 may allow to discriminate whether one or both of first capture zone 36A and second capture zone 36B is/are contaminated by metallic chips. For example, if resistor R1 and resistor R2 each have a resistance value of 2 k Ohms and none of first gap G1 and second gap G2 are electrically bridged by first chip 42A or second chip 42B (shown in FIG. 2A), resistance value RV between first output terminal 44A and second output terminal 44B will be about 4 k Ohms. However, if one of first gap G1 and second gap G2 is electrically bridged by first chip 42A or second chip 42B, resistance value RV between first output terminal 44A and second output terminal 44B will be about 2 k Ohms. If both first gap G1 and second gap G2 are electrically bridged by first chip 42A and second chip 42B respectively, resistance value RV between first output terminal 44A and second output terminal 44B will be about 0 Ohms (i.e., short circuit).

The configuration of MCD 228 may also be used to identify which one(s) of first capture zone 36A and second capture zone 36B is/are contaminated by metallic chips by using different resistance values of first resistor R1 and second resistor R2. This may be particularly useful if first gap G1 and second gap G2 are of different sizes and/or first capture zone 36A and second capture zone 36B are in different locations of lubrication system 20. For example, if first resistor R1 has a resistance value of 4 k Ohm and second resistor R2 has a resistance value of 2 k Ohm, and none of first gap G1 and second gap G2 are electrically bridged by first chip 42A or by second chip 42B (shown in FIG. 2A), resistance value RV between first output terminal 44A and second output terminal 44B will be about 6 k Ohms. However, if first gap G1 is electrically bridged by first chip 42A and second gap G2 is not electrically bridged by second chip 42B, resistance value RV between first output terminal 44A and second output terminal 44B will be about 2 k Ohms. If first gap G1 is not electrically bridged by first chip 42A and second gap G2 is electrically bridged by second chip 42B, resistance value RV between first output terminal 44A and second output terminal 44B will be about 4 k Ohms. If both first gap G1 and second gap G2 are electrically bridged by first chip 42A and second chip 42B respectively, resistance value RV between first output terminal 44A and second output terminal 44B will be about 0 Ohms (i.e., short circuit).

Controller 32 can then use the single resistance value RV to assess whether a small chip has been detected, a large chip has been detected, or if both first gap G1 and second gap G2 are electrically bridged by first chip 42A and second chip 42B respectively. This approach of discriminating between which capture zone(s) is causing the detection may be extended to MCDs of three or more detection zones.

In various embodiments disclosed herein, the single resistance value RV may provide a single and informative input to controller 32 and allow controller 32 to determine the state of MCD 228. For example, resistance value RV may be the sole piece of information transferred from MCD 228 to controller 32. Controller 32 may then use resistance value RV with one or more rules available to controller 32 to determine whether annunciation 46 is warranted. The rules may include actions associated with predetermined values for resistance value RV or predetermined ranges of values for resistance value RV. The rules and the multiple capture zones may be selected to provide a sensitivity suitable for providing legitimate chip detections and annunciations 46.

The use of the single input may also facilitate integration of MCD 228 and other magnetic chip detectors disclosed herein with new or existing aircraft engines. For example, the retrofitting of MCD 228 into engine 10 may require little to no hardware modifications, but may require software modifications to apply rules and carry out desired actions based on resistance value RV.

Figure 5A:
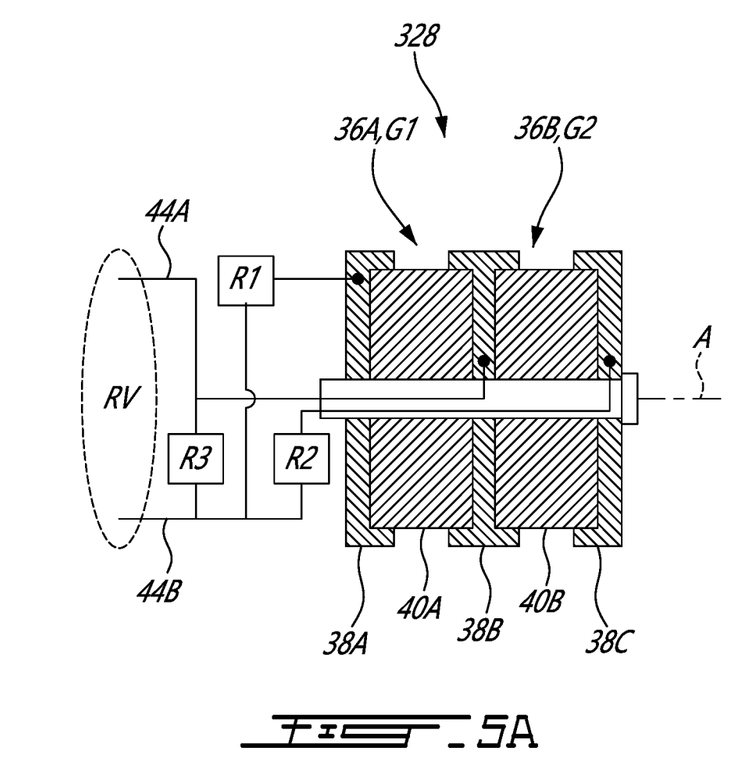
FIG. 5A is a schematic axial cross-section view of another exemplary multi-zone magnetic chip detector of the engine of FIG. 1.
Figure 5B:
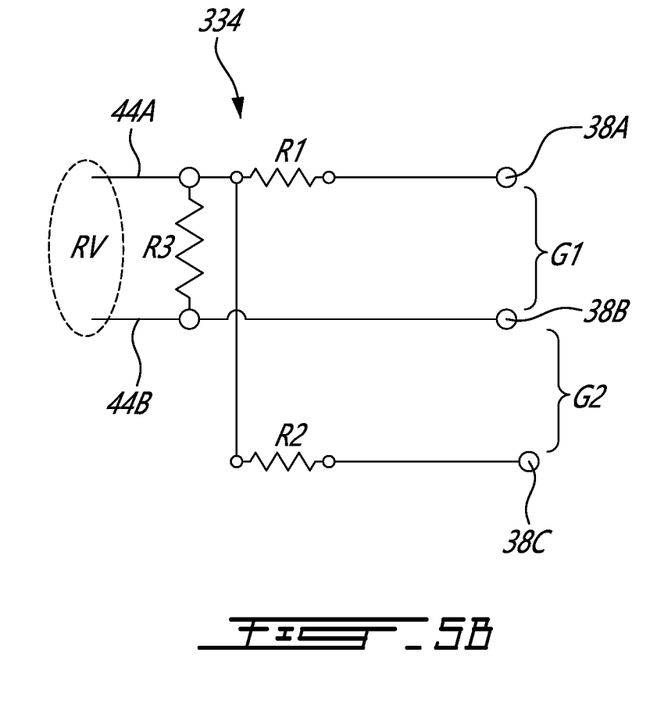
FIG. 5B is a schematic representation of an electric circuit associated with the multi-zone magnetic chip detector of FIG. 5A.

FIG. 5A is a schematic axial cross-section view of another exemplary multi-zone MCD 328 which may be part of chip detection system 30 of engine 10, and FIG. 5B is a schematic representation of electric circuit 334 associated with MCD 328. MCD 328 may have elements in common with other MCDs described above and like elements are identified using like reference numerals. First capture zone 36A of MCD 328 may include first MCD terminal 38A spaced apart from second MCD terminal 38B to define first gap G1 therebetween. Second capture zone 36B may include third MCD terminal 38C spaced apart from second MCD terminal 38B to define second gap G2 therebetween. In various embodiments, first gap G1 and second gap G2 may be disposed in parallel as shown in FIGS. 5A, 5B, or may be disposed in series in electric circuit 334. MCD 328 may be an axial disk-type magnetic chip detector. In some embodiments, first gap G1 and second gap G2 may be of substantially the same size. However, in other embodiments, first gap G1 and second gap G2 may be of different sizes depending on the size(s) of first chip 42A and of second chip 42B that are of interest. MCD 328 may include three or more capture zones defining respective gaps disposed in parallel or in series.

In contrast with MCD 228, MCD 328 may include first shunt resistor R1 disposed in series with first gap G1, second shunt resistor R2 disposed in series with second gap G2, and third shunt resistor R3 disposed in parallel with both first gap G1 and second gap G2.

During operation of MCD 328 when MCD 328 is immersed in lubricating fluid 26, the resultant resistance value RV may be indicative of which one(s) of first gap G1 and second gap G2 is/are electrically bridged by first chip 42A and/or second chip 42B based on which combination of first resistor R1, second resistor R2, third resistor R3, electrically bridged first gap G1, and electrically bridged second gap G2 are reflected in resistance value RV. Accordingly, the chip detection at MCD 328 may be detected by way of a change in resistance value RV which may be determined at controller 32. Upon detection of the change in resistance value RV that is indicative of a legitimate chip detection, controller 32 may initiate annunciation 46 which may alert a pilot of the aircraft and/or another interested party.

In various embodiments first capture zone 36A and second capture zone 36B may be in fluid communication with each other during operation. Alternatively, first capture zone 36A and second capture zone 36B may be fluidly sealed from each other and disposed in different fluid streams or in different fluid systems of engine 10.

Figure 6A:
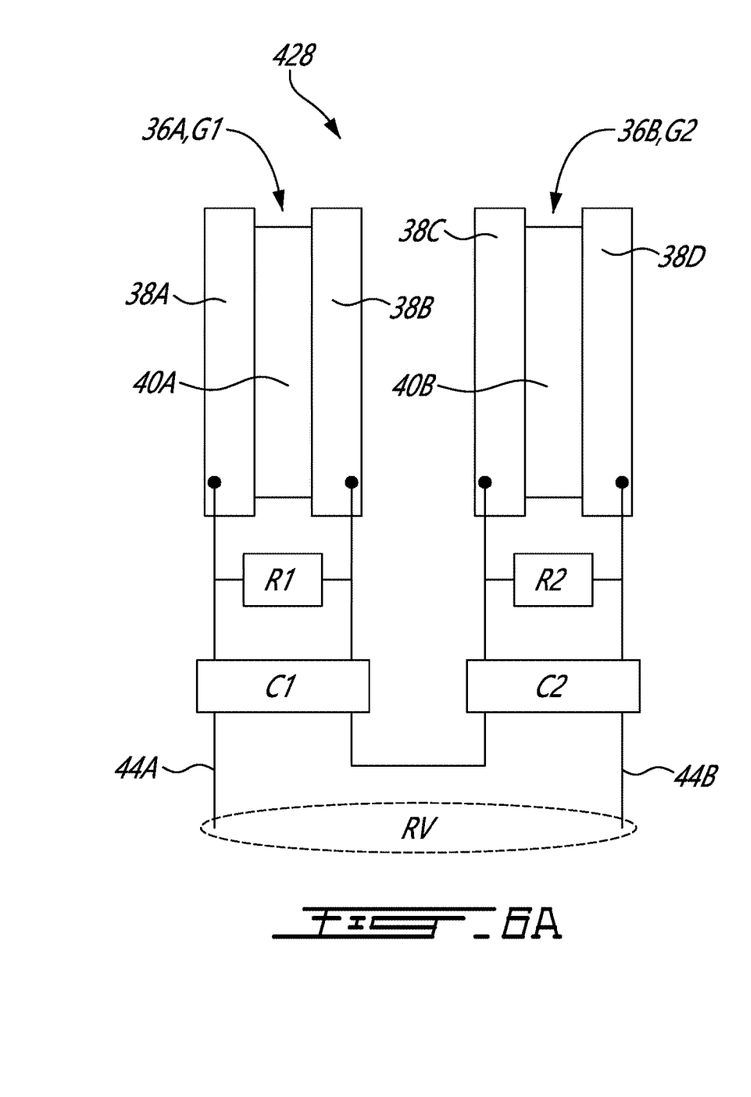
FIG. 6A is a schematic representation of another exemplary multi-zone magnetic chip detector of the engine of FIG. 1.
Figure 6B:
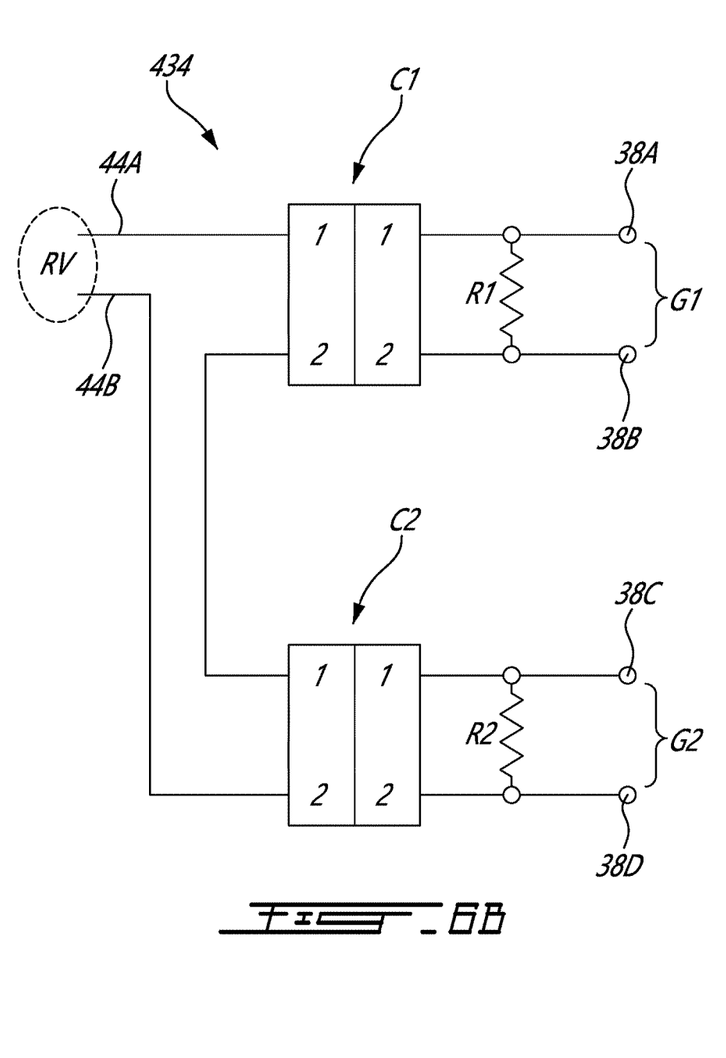
FIG. 6B is a schematic representation of an electric circuit associated with the multi-zone magnetic chip detector of FIG. 6A.

FIG. 6A is a schematic representation of another exemplary multi-zone MCD 428 of which may be part of chip detection system 30 of engine 10, and FIG. 6B is a schematic representation of electric circuit 434 associated with MCD 428. MCD 428 may have elements in common with other MCDs described above and like elements are identified using like reference numerals. First capture zone 36A of MCD 428 may include first MCD terminal 38A spaced apart from second MCD terminal 38B to define first gap G1 therebetween. Second capture zone 36B may include third MCD terminal 38C spaced apart from fourth MCD terminal 38D to define second gap G2 therebetween. In various embodiments, first gap G1 and second gap G2 may be disposed in series as shown in FIGS. 6A, 6B, or may be disposed in parallel in electric circuit 434. In some embodiments, first gap G1 and second gap G2 may be of substantially the same size. However, in other embodiments, first gap G1 and second gap G2 may be of different sizes depending on the size(s) of first chip 42A and of second chip 42B that are of interest.

MCD 428 may be a combination of two or more single-zone axial disk-type magnetic chip detectors that are daisy chained together. For example, first capture zone 36A may be provided by a first magnetic chip detector electrically integrated into electric circuit 434 via first connector C1, and second capture zone 36B may be provided by a second magnetic chip detector electrically integrated into electric circuit 434 via second connector C2. In some installations, first capture zone 36A and second capture zone 36B may be in fluid communication with each other during operation. Alternatively, first capture zone 36A and second capture zone 36B may be fluidly sealed from each other and disposed in different fluid streams or in different fluid systems of engine 10. The configuration of MCD 428 may permit the monitoring of different regions of lubrication system 20 using the single interface providing resistance value RV. The configuration of MCD 428 may permit a combination of different types of single-zone and/or multi-zone MCDs to be daisy chained together and provide a single output. For example, MCDs of different configurations (e.g., axial disk-type and prong type) and/or of different gap sizes may be combined together to meet requirements of the specific application.

MCD 428 may include first shunt resistor R1 disposed in parallel with first gap G1, and second shunt resistor R2 disposed in parallel with second gap G2.

During operation of MCD 428 when MCD 428 is immersed in lubricating fluid 26, the resultant resistance value RV may be indicative of which one(s) of first gap G1 and second gap G2 is/are electrically bridged by first chip 42A and/or second chip 42B based on which combination of first resistor R1, second resistor R2, electrically bridged first gap G1, and electrically bridged second gap G2 are reflected in resistance value RV.

Figure 7A:
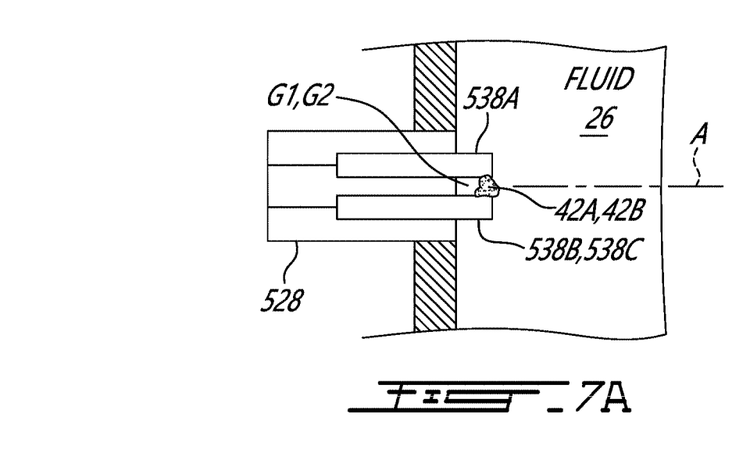
FIG. 7A is a schematic side view of another exemplary multi-zone magnetic chip detector of the engine of FIG. 1.
Figure 7B:
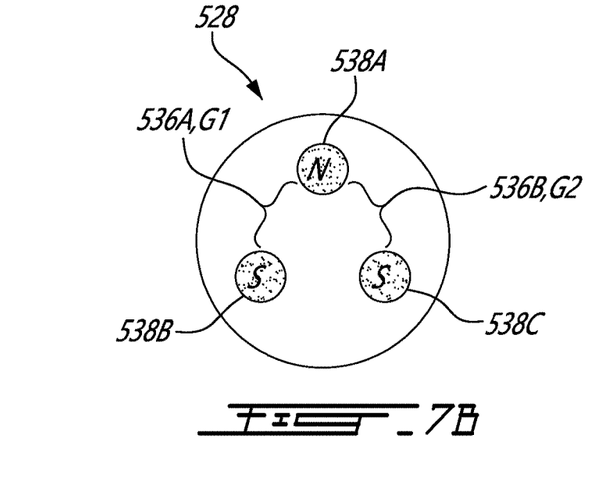
FIG. 7B is a schematic axial end-on view of the multi-zone magnetic chip detector of FIG. 7A.
Figure 7C:
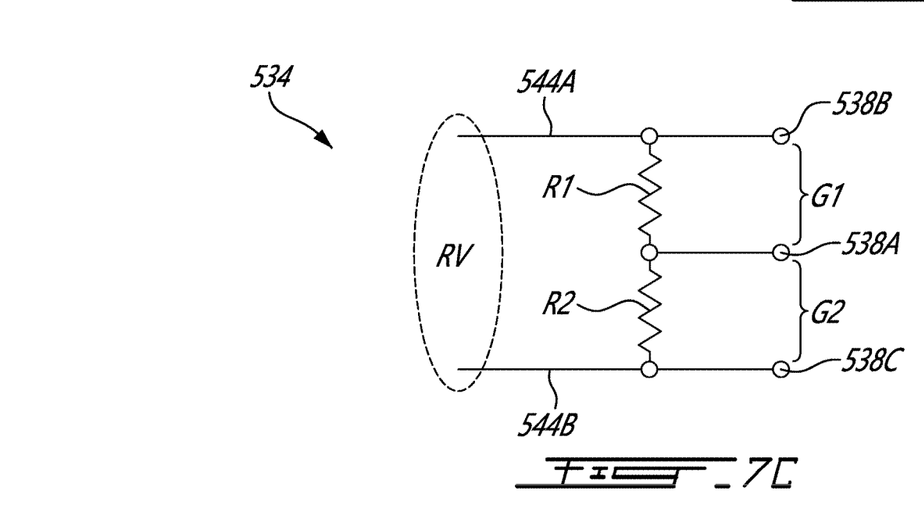
FIG. 7C is a schematic representation of an electric circuit associated with the multi-zone magnetic chip detector of FIG. 7A.

FIG. 7A is a schematic representation of another exemplary multi-zone MCD 528 of which may be part of chip detection system 30 of engine 10. MCD 528 may be a prong-type magnetic chip detector. FIG. 7B is a schematic axial end-on view of MCD 528 looking at MCD 528 along axis A in FIG. 7A. FIG. 7C is a schematic representation of electric circuit 534 associated with MCD 528 of FIG. 7A. First capture zone 536A of MCD 528 may include first MCD terminal 538A spaced apart from second MCD terminal 538B to define first gap G1 therebetween. First MCD terminal 538A may be a magnetic prong having properties of a magnet and having a north (N) polarity. Second MCD terminal 538B may be a magnetic prong having properties of a magnet and having a south (S) polarity. Second capture zone 536B may include third MCD terminal 538C spaced apart from first MCD terminal 538A to define second gap G2 therebetween. Third MCD terminal 538C may be a magnetic prong having properties of a magnet and having a south (S) polarity. As shown in FIG. 7B, first MCD terminal 538A, second MCD terminal 538B, and third MCD terminal 538C may be disposed in a triangular formation. A gap between two neighboring prongs of the same polarity such as between second MCD terminal 538B and third MCD terminal 538C, which are both south pole prongs, will not be a capture zone since the magnetic chips on prongs of the same polarity will repel each other.

In various embodiments, first gap G1 and second gap G2 may be disposed in series as shown in FIG. 7C or may be disposed in parallel in electric circuit 534. In some embodiments, first gap G1 and second gap G2 may be of substantially the same size. However, in other embodiments, first gap G1 and second gap G2 may be of different sizes depending on the size(s) of first chip 42A and of second chip 42B that are of interest. MCD 528 may include first shunt resistor R1 disposed in parallel with first gap G1, and second shunt resistor R2 disposed in parallel with second gap G2.

During operation of MCD 528 when MCD 528 is immersed in lubricating fluid 26, the resultant resistance value RV may be indicative of which one(s) of first gap G1 and second gap G2 is/are electrically bridged by first chip 42A and/or second chip 42B based on which combination of first resistor R1, second resistor R2, electrically bridged first gap G1, and electrically bridged second gap G2 are reflected in resistance value RV between first output terminal 544A and second output terminal 544B.

Figure 8A:
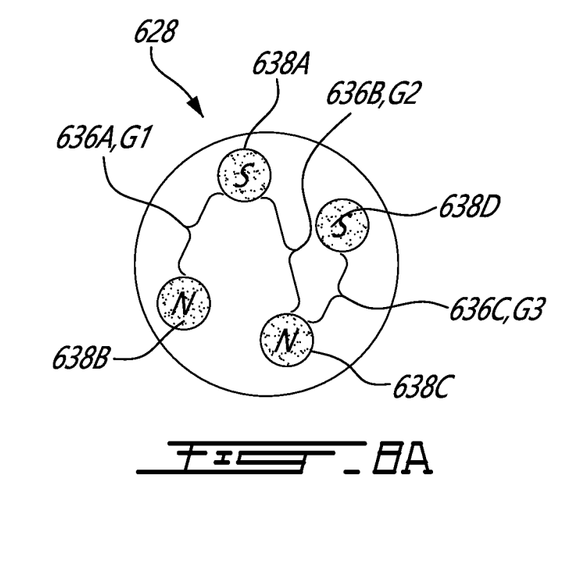
FIG. 8A is a schematic axial end-on view of another exemplary multi-zone magnetic chip detector of the engine of FIG. 1.
Figure 8B:
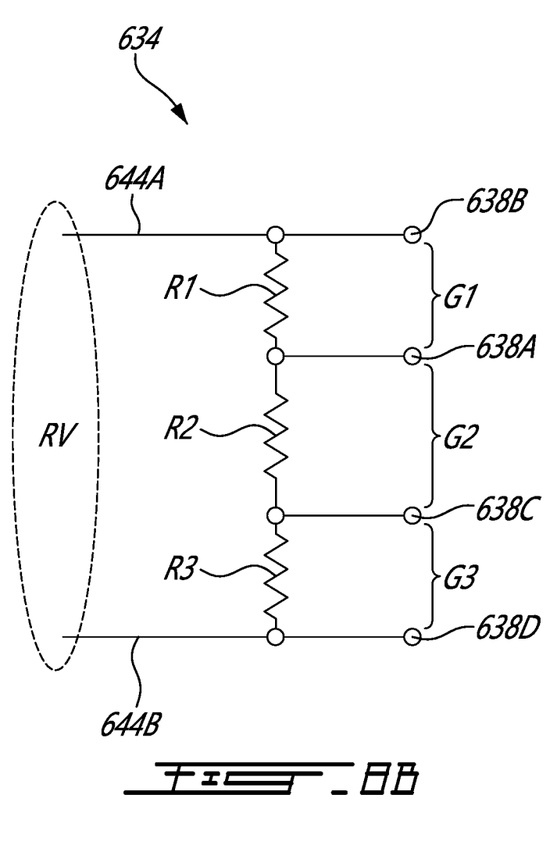
FIG. 8B is a schematic representation of an electric circuit associated with the multi-zone magnetic chip detector of FIG. 8A.

FIG. 8A is a schematic axial end-on view of another exemplary multi-zone MCD 628 which may be part of chip detection system 30 of engine 10. FIG. 8B is a schematic representation of electric circuit 634 associated with MCD 628 of FIG. 8A. First capture zone 636A of MCD 628 may include first MCD terminal 638A spaced apart from second MCD terminal 638B to define first gap G1 therebetween. First MCD terminal 638A may be a magnetic prong having properties of a magnet and having a south (S) polarity. Second MCD terminal 638B may be a magnetic prong having properties of a magnet and having a north (N) polarity. Second capture zone 636B may include third MCD terminal 638C spaced apart from first MCD terminal 638A to define second gap G2 therebetween. Third MCD terminal 638C may be a magnetic prong having properties of a magnet and having a north (N) polarity. Third capture zone 636C may include third MCD terminal 638C spaced apart from fourth MCD terminal 638D to define third gap G3 therebetween. Fourth MCD terminal 638D may be a magnetic prong having properties of a magnet and having a south (S) polarity. As shown in FIG. 8A, first MCD terminal 638A, second MCD terminal 638B, third MCD terminal 638C, and fourth MCD terminal 638D may be disposed in a rectangular or square formation. A gap between two neighboring prongs of the same polarity will not be a capture zone since the magnetic chips on prongs of the same polarity will repel each other.

In various embodiments, first gap G1, second gap G2, and third gap G3 may be disposed in series as shown in FIG. 8B, or may be disposed in parallel in electric circuit 634. In some embodiments, first gap G1, second gap G2, and third gap G3 may be of substantially the same size. However, in other embodiments, first gap G1, second gap G2, and third gap G3 may be of different sizes depending on the size(s) of chips that are of interest. For example, second gap G2 may be larger than first gap G1 and also larger than third gap G3 as shown in FIG. 8B. MCD 628 may include first shunt resistor R1 disposed in parallel with first gap G1, second shunt resistor R2 disposed in parallel with second gap G2, and third shunt resistor R3 disposed in parallel with third gap G3.

During operation of MCD 628 when MCD 628 is immersed in lubricating fluid 26, the resultant resistance value RV may be indicative of which one(s) of first gap G1, second gap G2, and third gap G3 is/are electrically bridged by chips based on which combination of first resistor R1, second resistor R2, third resistor R3, electrically bridged first gap G1, electrically bridged second gap G2, and electrically bridged third gap G3 are reflected in resistance value RV between first output terminal 644A and second output terminal 644B.

Figure 9A:
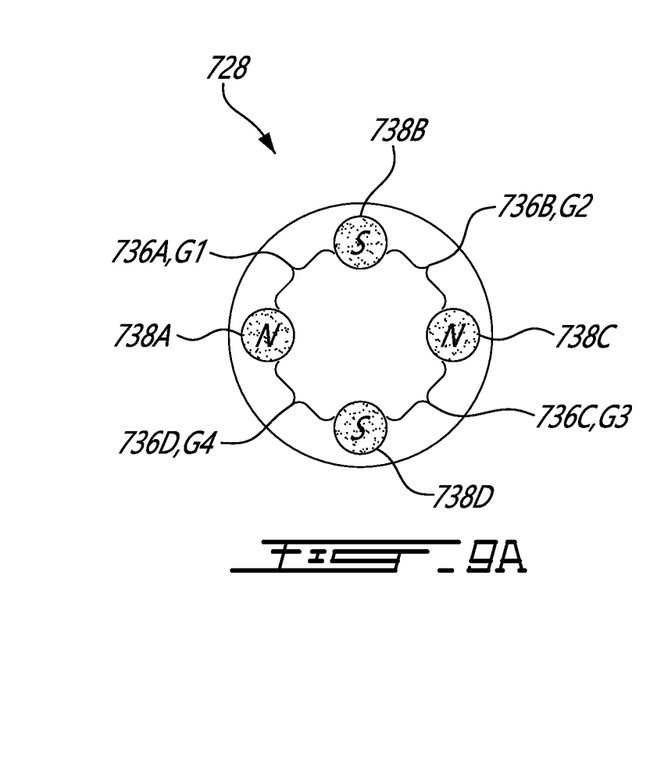
FIG. 9A is a schematic axial end-on view of another exemplary multi-zone magnetic chip detector of the engine of FIG. 1.
Figure 9B:
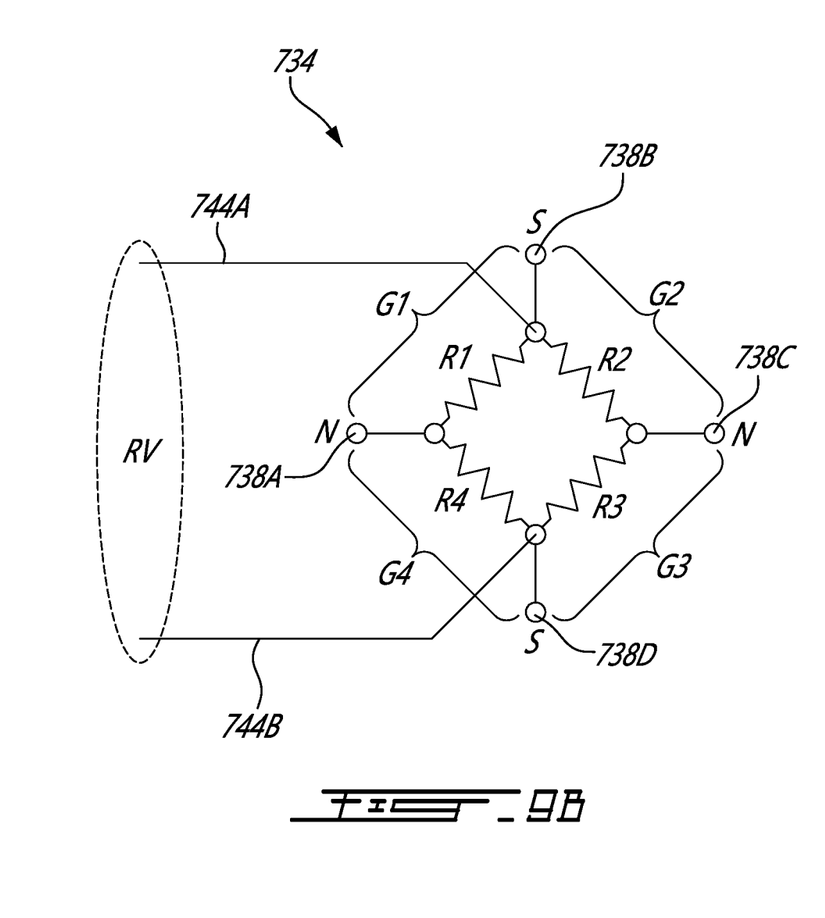
FIG. 9B is a schematic representation of an electric circuit associated with the multi-zone magnetic chip detector of FIG. 9A.

FIG. 9A is a schematic axial end-on view of another exemplary multi-zone MCD 728 which may be part of chip detection system 30 of engine 10. FIG. 9B is a schematic representation of electric circuit 734 associated with MCD 728 of FIG. 9A. First capture zone 736A of MCD 728 may include first MCD terminal 738A spaced apart from second MCD terminal 738B to define first gap G1 therebetween. First MCD terminal 738A may be a magnetic prong having properties of a magnet and having a north (N) polarity. Second MCD terminal 738B may be a magnetic prong having properties of a magnet and having a south (S) polarity. Second capture zone 736B may include third MCD terminal 738C spaced apart from second MCD terminal 738B to define second gap G2 therebetween. Third MCD terminal 738C may be a magnetic prong having properties of a magnet and having a north (N) polarity. Third capture zone 736C may include third MCD terminal 738C spaced apart from fourth MCD terminal 738D to define third gap G3 therebetween. Fourth MCD terminal 738D may be a magnetic prong having properties of a magnet and having a south (S) polarity. Fourth capture zone 736D may include first MCD terminal 738A spaced apart from fourth MCD terminal 738D to define fourth gap G4 therebetween. As shown in FIG. 9A, first MCD terminal 738A, second MCD terminal 738B, third MCD terminal 738C, and fourth MCD terminal 738D may be disposed in a rectangular or square formation.

In some embodiments, first gap G1 and fourth gap G4 may be disposed in series, and second gap G2 and third gap G3 may be disposed in series in electric circuit 734. A first branch including first gap G1 and fourth gap G4 may be disposed in parallel with a second branch including second gap G2 and third gap G3. In some embodiments, first gap G1, second gap G2, third gap G3 and fourth gap G4 may be of substantially the same size. However, in other embodiments, first gap G1, second gap G2, third gap G3, and fourth gap G4 may be of different sizes depending on the size(s) of chips that are of interest. MCD 728 may include first shunt resistor R1 disposed in parallel with first gap G1, second shunt resistor R2 disposed in parallel with second gap G2, third shunt resistor R3 disposed in parallel with third gap G3, and fourth shunt resistor R4 disposed in parallel with fourth gap G4. In some embodiments, first resistor R1, second resistor R2, third resistor R3, and fourth resistor R4 may be connected in a Wheatstone bridge configuration.

During operation of MCD 728 when MCD 728 is immersed in lubricating fluid 26, the resultant resistance value RV between first output terminal 744A and second output terminal 744B may be near 0 Ohms (i.e., short circuit) when two or three of first gap G1, second gap G2, third gap G3, and fourth gap G4 are electrically bridged by metallic chips.

Figure 10:
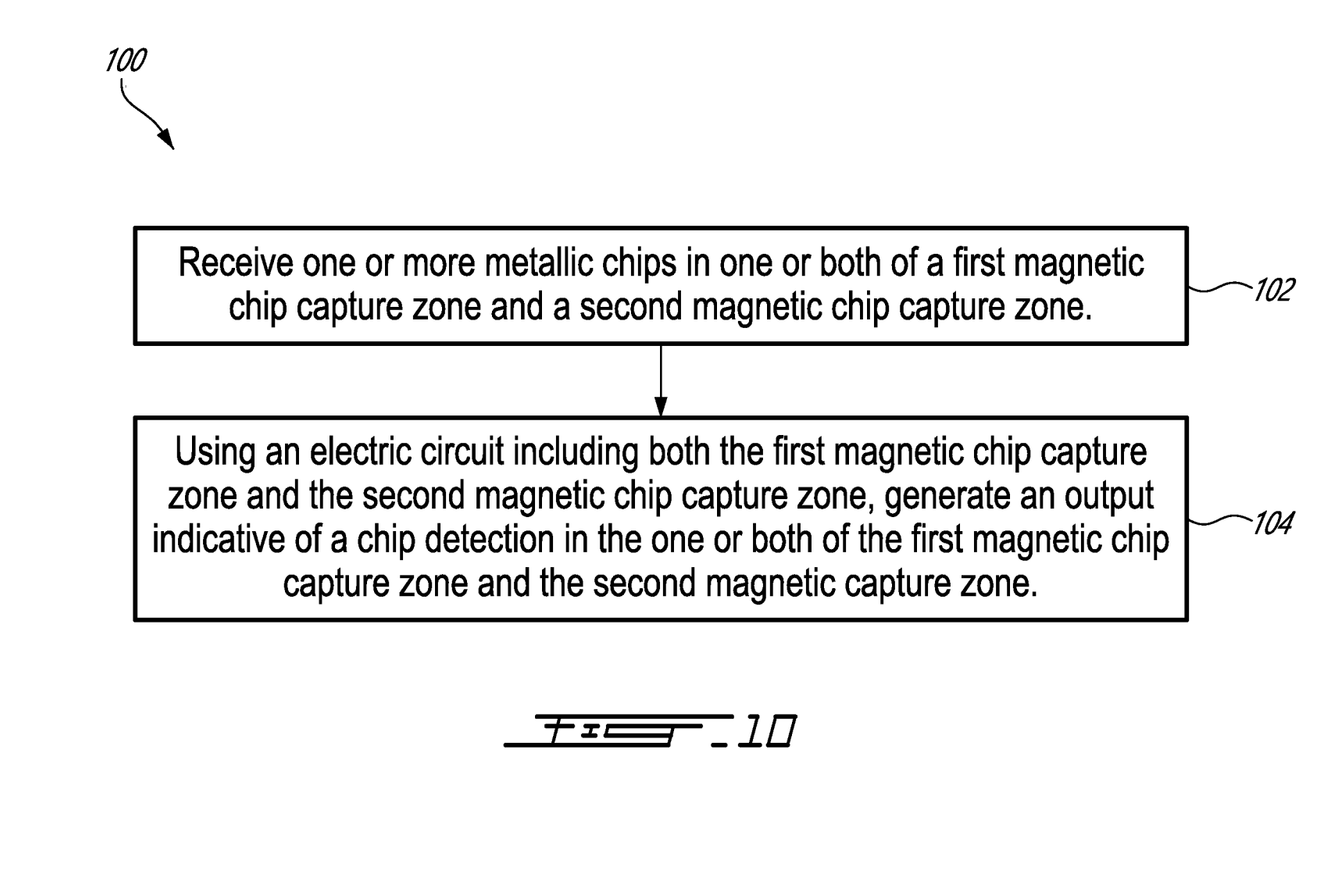
FIG. 10 is a flow diagram of a method of detecting metallic chips in engine fluid of an engine.

FIG. 10 is a flow diagram of method 100 of detecting metallic chips in engine fluid of an engine. Method 100 may be performed using MCD 28,128,228, 328, 428, 528, 628, 728 described herein or using another MCD. Aspects of method 100 may be combined with other methods or steps described herein. Method 100 may also include aspects of system 30 and of MCD 28,128,228, 328, 428, 528, 628, 728. In various embodiments, method 100 may include:

when the magnetic chip detector (e.g., MCD 28,128,228, 328, 428, 528, 628, 728) is immersed in engine fluid (e.g., lubricating fluid 26), receiving one or more metallic chips (e.g., 42A, 42B) in one or both of the first magnetic chip capture zone and the second magnetic chip capture zone (block 102); and using an electric circuit (e.g., electric circuit 34,134,234, 334, 434, 534, 634, 734) including both the first magnetic chip capture zone and the second magnetic chip capture zone, generating an output indicative of a chip detection in the one or both of the first magnetic chip capture zone and the second magnetic capture zone (block 104).

In some embodiments of method 100, the output may be indicative of which of the first magnetic chip capture zone, the second magnetic capture zone, or optionally one or more additional magnetic chip capture zones is/are associated with the chip detection. In some embodiments of method 100, the first magnetic chip capture zone and the second magnetic chip capture zone may be in fluid communication with each other when receiving one or more metallic chips in one or both of the first magnetic chip capture zone and the second magnetic chip capture zone.

The embodiments described in this document provide non-limiting examples of possible implementations of the present technology. Upon review of the present disclosure, a person of ordinary skill in the art will recognize that changes may be made to the embodiments described herein without departing from the scope of the present technology.

What is claimed is:

1. A multi-zone magnetic chip detector for detecting chips in lubricating fluid of an engine, the multi-zone magnetic chip detector comprising:
   a first magnetic chip capture zone including a first electrically conductive terminal spaced apart from a second electrically conductive terminal to define a first chip-receiving gap therebetween;
   a second magnetic chip capture zone including a third electrically conductive terminal and either the second electrically conductive terminal or a fourth electrically conductive terminal to define a second chip-receiving gap therebetween; and
   an electric circuit including both the first chip-receiving gap and the second chip-receiving gap, the electric circuit providing an output indicative of a chip detection by one or both of the first magnetic chip capture zone and the second magnetic capture zone.

2. The multi-zone magnetic chip detector as defined in claim 1, wherein the second magnetic chip capture zone includes the third electrically conductive terminal and the second electrically conductive terminal.

3. The multi-zone magnetic chip detector as defined in claim 1, wherein the electric circuit includes the first chip-receiving gap and the second chip-receiving gap disposed in series.

4. The multi-zone magnetic chip detector as defined in claim 3, wherein the electric circuit includes a resistor disposed in parallel with both the first chip-receiving gap and the second chip-receiving gap.

5. The multi-zone magnetic chip detector as defined in claim 3, wherein the electric circuit includes a first resistor disposed in parallel with the first chip-receiving gap.

6. The multi-zone magnetic chip detector as defined in claim 5, wherein the electric circuit includes a second resistor disposed in parallel with the second chip-receiving gap.

7. The multi-zone magnetic chip detector as defined in claim 6, wherein the first resistor and the second resistor have different resistance values.

8. The multi-zone magnetic chip detector as defined in claim 1, wherein the electric circuit includes the first chip-receiving gap and the second chip-receiving gap disposed in parallel.

9. The multi-zone magnetic chip detector as defined in claim 8, wherein:
   the electric circuit includes a first resistor disposed in series with the first chip-receiving gap; and
   the electric circuit includes a second resistor disposed in series with the second chip-receiving gap.

10. The multi-zone magnetic chip detector as defined in claim 1, wherein the second magnetic chip capture zone includes the third electrically conductive terminal and the fourth electrically conductive terminal.

11. The multi-zone magnetic chip detector as defined in claim 1, wherein:
    a first magnet is disposed between the first electrically conductive terminal and the second electrically conductive terminal; and
    a second magnet is disposed between the third electrically conductive terminal and either the second electrically conductive terminal or the fourth electrically conductive terminal.

12. The multi-zone magnetic chip detector as defined in claim 11, wherein:
    the second magnetic chip capture zone includes the third electrically conductive terminal and the second electrically conductive terminal; and
    the first electrically conductive terminal, the second electrically conductive terminal, the third electrically conductive terminal, the first magnet and the second magnet are disc-shaped and coaxial.

13. The multi-zone magnetic chip detector as defined in claim 1, wherein:
    the second magnetic chip capture zone includes the third electrically conductive terminal and the second electrically conductive terminal; and
    the first electrically conductive terminal, the second electrically conductive terminal, and the third electrically conductive terminal are magnetic prongs.

14. The multi-zone magnetic chip detector as defined in claim 13, wherein the first electrically conductive terminal, the second electrically conductive terminal, and the third electrically conductive terminal are disposed in a triangular formation.

15. The multi-zone magnetic chip detector as defined in claim 13, comprising:
    a third magnetic chip capture zone including the third electrically conductive terminal and the fourth electrically conductive terminal to define a third chip-receiving gap therebetween; and
    a fourth magnetic chip capture zone including the fourth electrically conductive terminal and the first electrically conductive terminal to define a fourth chip-receiving gap therebetween;

wherein:
the circuit includes: a first resistor disposed in parallel with the first chip-collecting gap; a second resistor disposed in parallel with the second chip-collecting gap; a third resistor disposed in parallel with the third chip-collecting gap; and fourth resistor disposed in parallel with the fourth chip-collecting gap; and
the first resistor, the second resistor, the third resistor and the fourth resistor are connected in a Wheatstone bridge configuration.

16. The multi-zone magnetic chip detector as defined in claim 1, wherein the first chip-collecting gap is larger than the second chip-collecting gap.

17. An aircraft engine comprising:
a lubrication system for distributing lubricating fluid to one or more lubrication loads; and
a multi-zone magnetic chip detector immersed in the lubricating fluid, the multi-zone magnetic chip detector including:
a first magnetic chip capture zone including a first electrically conductive terminal spaced apart from a second electrically conductive terminal to define a first chip-receiving gap therebetween;
a second magnetic chip capture zone including a third electrically conductive terminal and either the second electrically conductive terminal or a fourth electrically conductive terminal to define a second chip-receiving gap therebetween; and
an electric circuit including both the first chip-receiving gap and the second chip-receiving gap, the electric circuit providing an output indicative of a chip detection by one or both of the first magnetic chip capture zone and the second magnetic capture zone.

18. The aircraft engine as defined in claim 17, wherein:
the second magnetic chip capture zone includes the third electrically conductive terminal and the second electrically conductive terminal;
the electric circuit includes the first chip-receiving gap and the second chip-receiving gap disposed in series; and
the electric circuit includes a first resistor disposed in parallel with the first chip-receiving gap.

19. The aircraft engine as defined in claim 17, wherein:
the second magnetic chip capture zone includes the fourth electrically conductive terminal and the third electrically conductive terminal;
the electric circuit includes the first chip-receiving gap and the second chip-receiving gap disposed in parallel; and
the electric circuit includes a first resistor disposed in parallel with the first chip-receiving gap.

20. A method of detecting metallic chips in engine fluid of an engine using a multi-zone magnetic chip detector including: a first magnetic chip capture zone defined between a first electrically conductive terminal and a second electrically conductive terminal; and a second magnetic chip capture zone defined between a third electrically conductive terminal and either the second electrically conductive terminal or a fourth electrically conductive terminal, the method comprising:
when the multi-zone magnetic chip detector is immersed in engine fluid, receiving one or more metallic chips in one or both of the first magnetic chip capture zone and the second magnetic chip capture zone; and
using an electric circuit including both the first magnetic chip capture zone and the second magnetic chip capture zone, generating, by the electric circuit, an output indicative of a chip detection in the one or both of the first magnetic chip capture zone and the second magnetic capture zone.

* * * * *